US008045773B2

(12) United States Patent
Lautenschläger

(10) Patent No.: US 8,045,773 B2
(45) Date of Patent: Oct. 25, 2011

(54) METHOD FOR SEGMENTING A MYOCARDIAL WALL AND DEVICE FOR DETECTING A CORONARY ARTERY WITH PATHOLOGICAL CHANGES

(75) Inventor: Stefan Lautenschläger, Hausen (DE)

(73) Assignee: Siemens Aktiengesellschaft, Munich (DE)

( * ) Notice: Subject to any disclaimer, the term of this patent is extended or adjusted under 35 U.S.C. 154(b) by 792 days.

(21) Appl. No.: 12/214,972

(22) Filed: Jun. 24, 2008

(65) Prior Publication Data
US 2009/0003680 A1    Jan. 1, 2009

(30) Foreign Application Priority Data
Jun. 28, 2007  (DE) .......................... 10 2007 029 886

(51) Int. Cl.
*G06K 9/00*  (2006.01)
(52) U.S. Cl. .................................................. 382/128
(58) Field of Classification Search .............. 382/128, 382/173
See application file for complete search history.

(56) References Cited

U.S. PATENT DOCUMENTS
7,627,078 B2 * 12/2009 Hsieh et al. .................... 378/4
2005/0059876 A1 *  3/2005 Krishnan et al. ............ 600/407
2006/0122500 A1 *  6/2006 Heismann et al. .......... 600/425
2007/0238968 A1 * 10/2007 Rappoport et al. .......... 600/407

FOREIGN PATENT DOCUMENTS
DE    10 2004 055 460 A1    4/2008

OTHER PUBLICATIONS
Flohr et al., Computer Tomography, "First Performance Evaluation of a dual-source CT (DSCT) System", Eur Radiol, 2006, pp. 256-268, vol. 16., Springer-Verlag.
Cerqueira et al., "Circulation", Journal of the American Heart Association, 2002, pp. 538-542, Internet: http://circ.ahajournals.org/cgi/content/full/105/4/539, Retrieved from Internet Mar. 3, 2008, ISSN: 1524-4539.

* cited by examiner

*Primary Examiner* — W. B. Perkey

(57) ABSTRACT

The present invention relates to a method for segmenting a myocardial wall with the following steps: recording a first data record and a second data record in the same cardiac phase by means of x-ray radiation with differing radiation intensities, reconstructing the myocardial wall from the first and second data record. To generate a detailed and complete reconstruction of the myocardial wall, it is proposed that the method be supplemented by the following steps: separating an inside and an outside of the myocardial wall from the data record recorded with higher radiation intensity, and separating tissue interspersing the myocardial wall between the inside and the outside, in particular fatty tissue, from the data record recorded with lower radiation intensity.

12 Claims, 2 Drawing Sheets

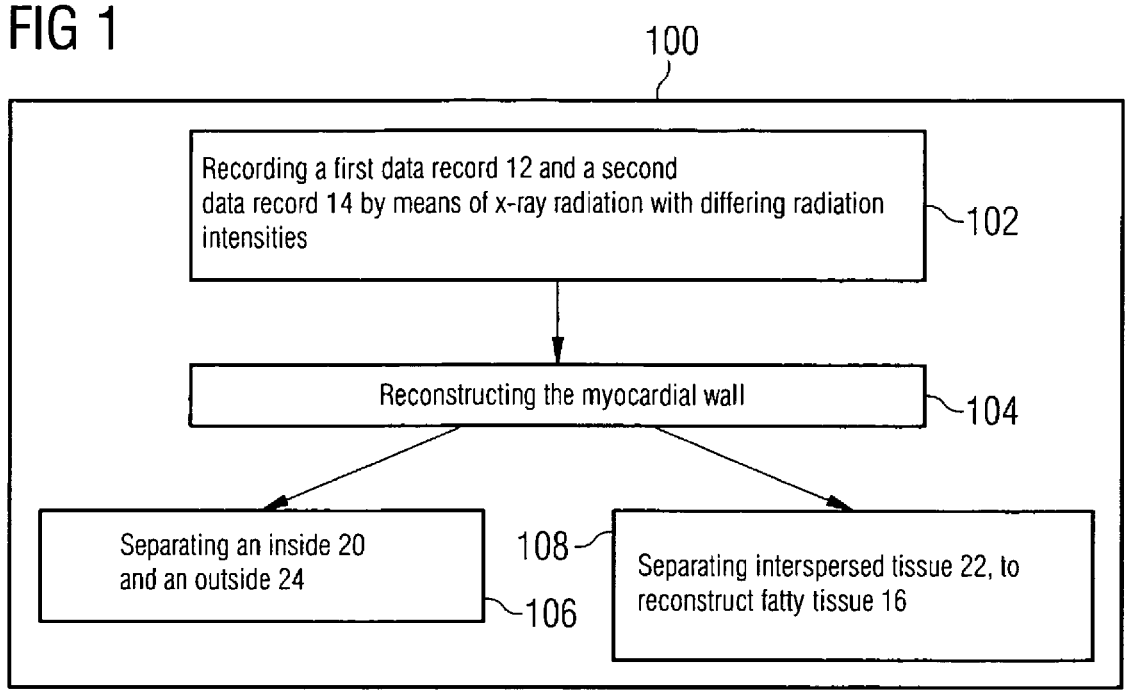
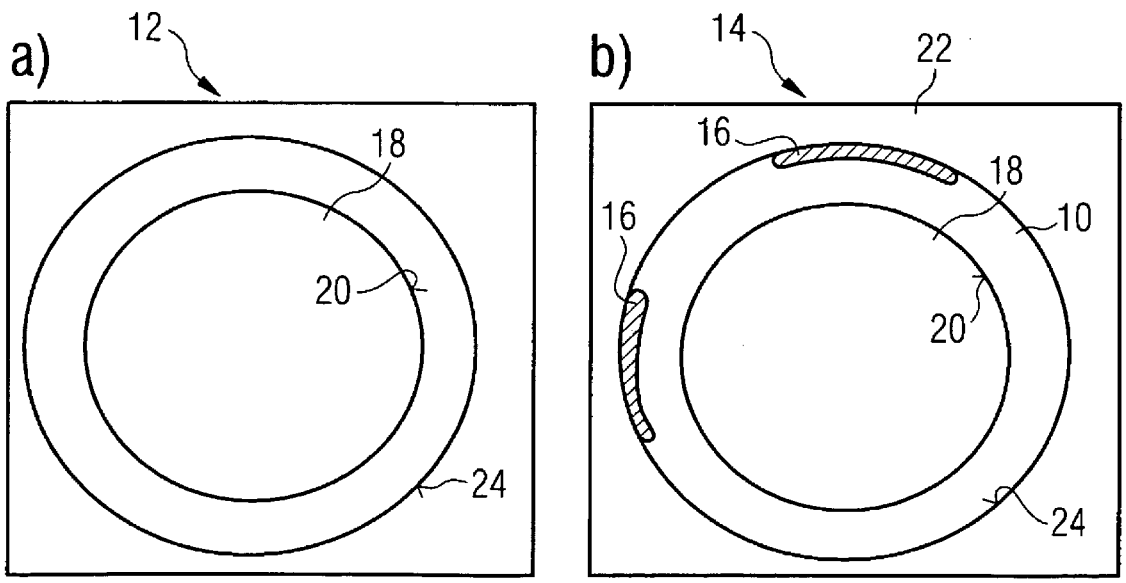

METHOD FOR SEGMENTING A MYOCARDIAL WALL AND DEVICE FOR DETECTING A CORONARY ARTERY WITH PATHOLOGICAL CHANGES

CROSS REFERENCE TO RELATED APPLICATIONS

This application claims priority of German application No. 10 2007 029 886.4 filed Jun. 28, 2007, which is incorporated by reference herein in its entirety.

FIELD OF THE INVENTION

The present invention relates to a method for segmenting a myocardial wall and a device for detecting a coronary artery with pathological changes.

BACKGROUND OF THE INVENTION

A generic method, in particular using an x-ray tomograph with two x-ray beam sources is known from the publication "First performance evaluation of a dual-source CT (DSCT) system" by Flohr et al., which appeared in Eur. Radiol. 2006, 16, pages 256 to 268.

By recording a first data record and a second data record of the myocardial wall in the same cardiac phase by means of x-ray radiation with differing radiation intensities, the myocardial wall is segmented by the first data record and the second data record. However a corresponding image comprises only an external outline of the myocardial wall and shows the coronary arteries.

Current studies show that cardiological diseases are constantly on the increase. There is therefore a need to identify possible pathological changes, stenoses, constrictions, etc, as early as possible. There is therefore an emphasis on segmenting the pump function of the heart and in this process principally that of the left chamber, the so-called ventricle and its myocardial wall, the myocardium. Stenosed or calcified coronary arteries, which are no longer able to supply the myocardium with sufficient oxygen-rich blood, have the greatest negative effect on this pump function. As a result the muscle of the region supplied by the corresponding coronary artery is weakened and in time ceases to play an active role in the contracting movement, thereby weakening cardiac output. During the further course of the disease fat cells accumulate specifically at these less perfused points of the myocardium.

In current standard examinations coronary protocols are used, which set the dose of an x-ray tube of a CT scanner so that it is possible to achieve an optimum contrast between the lightness of the interiors of the coronary arteries filled with contrast agent and the darkness of external tissue. This standard protocol allows a distinction between contrast agent and tissue but makes a tissue classification between the myocardium and surrounding tissue, which is of interest for cardiological applications, virtually impossible. The reason for this is a relatively high x-ray tube voltage, typically approximately 120 kV, for recording a first data record.

In current cardiological examinations, such as induced computed tomography scans—abbreviated to CT scans—an attempt is made to find pathological changes to the coronary arteries by examining the coronary arteries themselves. In other words an attempt is made to find constrictions and stenoses or calcifications by tracking each individual coronary artery in the CT data and checking for pathological changes. This method has three significant disadvantages:

Firstly this method is very time-consuming, since every individual branch of the coronary arteries would have to be tracked in CT recordings. A large number of branches of the coronary arteries means a time outlay that is no longer reasonable. To manage this time outlay, frequently only a few main branches of the coronary arteries are examined, resulting in a greatly reduced probability of discovery. In other words the pathological changes are only identified very late and not at an initial stage, thereby resulting in a lower probability of recovery and serious and extremely cost-intensive delay consequences.

Secondly pathological changes in the coronary arteries that are present in the initial stage cannot be detected on the basis of examinations of the coronary arteries themselves.

SUMMARY OF THE INVENTION

The object of the present invention is therefore to achieve better visualization of the pump function of the heart.

According to the invention this object is achieved by the claims.

It has proven that it is possible to check pump function simply on the basis of a detailed visualization of the myocardial wall.

In order to be able to check pump function, a reliable segmentation of the myocardium, advantageously in different cardiac phases, is essential. An inside of the myocardial wall, which conveys blood during movement, should be segmented with higher radiation intensity by means of the first data record. If contrast agent is introduced into the blood flow when recording the first data record, the inside can be segmented particularly efficiently based on high weakening coefficients. The outside of the myocardial wall can also be segmented. The wall thickness that can be derived as a result is however only a rough measure of the strength of the myocardial wall. Generally the myocardial wall is surrounded by fatty tissue, with parts of it interspersed with fatty tissue, thereby reflecting a greater thickness of the muscular tissue.

The challenge is mainly to demarcate the myocardial tissue from the surrounding lung tissue and predominantly fatty tissue. This tissue classification is of the greatest benefit for reliable, automatic myocardial segmentation.

The myocardial/fatty tissue classification for optimum automatic segmentation of the myocardium is essentially performed using the second data record, which is provided for example by a dual energy CT scanner. The radiation intensity here is set so that it is possible to differentiate fatty tissue and myocardial wall. The reconstruction can be executed in the form of visualizations of a cross-section of the patient.

Because of the lower radiation intensity of the x-ray radiation used here, detailed structural information, for example fatty tissue on the outside of the myocardial wall, has to be visualized. It is therefore possible to determine the exact thickness of the myocardial wall, providing information about muscle proportion and its strength. Additional information about its blood supply can be read from the first data record.

The two data records obtained using the above-mentioned method allow segmentation with an automatic, computer-assisted evaluation tool. Taking into account information from both data records thus allows optimum segmentation of the myocardium. The imaging of the visualized myocardial wall can indicate deformations, anomalies, in particular its blood supply or perfusion. As a result the complex examination of the coronary arteries can be limited to specific branches. If the physician identifies reduced perfusion of the myocardium at a certain point, s/he can use his/her anatomical knowledge or computer assistance to identify the relevant coronary artery and carry out a more precise careful examination to find a corresponding pathological change. The length of the examination is significantly shortened, as the examining physician no longer has to track every individual coronary artery but can restrict him/herself to the branches which produce reduced perfusion of the myocardium or reduced wall movement.

The method is advantageously implemented in such a manner that an image of the myocardial wall is generated in the form of a longitudinal or short axis cross-section or a polar map. These images provide a cross-sectional view of the myocardial wall. It is also possible to determine the wall thickness of the myocardial wall. The polar map of the myocardial wall also allows a very simple and fast analysis of the image with regard to the perfusion of the myocardial wall. A color scale can be used so that the polar map can also show the wall thickness taking into account the fatty tissue of the myocardial wall.

To this end provision can be made according to a development of the inventive method for a series of first and second data records to be generated in different cardiac phases. These images can be recorded in particular with an ECG trigger, to generate an image of the myocardial wall at the end-diastolic and/or end-systolic point. These two extremes offer a reliable basis for checking the pump function of the heart. It is also possible to estimate a beat volume from these images. This myocardium, which is preferably segmented in a number of cardiac phases, can thus be examined very quickly and reliably in respect of the above problems relating to blood supply and wall movement.

A further object of the present invention is to specify a device, which provides early identification of coronary arteries with pathological changes.

With a dual-source CT scanner two x-ray tubes and two detectors assigned to their beam paths rotate about a patient. In order to be able to carry out the two above-mentioned classifications, the two x-ray tubes are operated at different voltages. The segmentation of blood containing contrast agent is achieved with a relatively high voltage, approximately 120 kV, while the classification of tissue as muscular tissue and fatty tissue should be carried out at lower voltage, approximately 80 kV. The two possible modes produce two data records containing different and complementary information.

Alternatively 3D rotational recordings via C-arm can be used. To this end an x-ray tube can be operated at respectively different voltages. A further x-ray tube with an assigned detector can also be added to record the second data record. The beam paths of the two x-ray tubes intersect a center point of a circle and are arranged with the detectors in a plane perpendicular to the axis of rotation.

In both instances two data records of the myocardial wall can be recorded simultaneously.

According to the invention the device has one movement profile each of a myocardial wall divided into segments. The movement profiles are derived from segmentations according to the method described above. At least one movement profile is separated, which differs from another movement profile. The other movement profile can be derived from an adjacent segment or can be stored by the device for comparison purposes. The stored movement profile can be an earlier recorded movement profile of the same myocardial wall or the movement profile of a healthy other person.

The difference two movement profiles of the myocardial wall for example indicates reduced perfusion of a segment. At least one coronary artery is assigned to this myocardial area with reduced movement capacity. This coronary artery shown in the image is marked. To this end the coronary artery can be visualized in color or parts of the myocardium can be highlighted in the image, for example by means of an arrow.

BRIEF DESCRIPTION OF THE DRAWINGS

Preferred exemplary embodiments of the invention are described below with reference to the accompanying drawings, in which:

FIG. 1 shows an exemplary embodiment of an inventive method for segmenting a myocardial wall;

FIG. 2a shows a reconstruction of a data record of the myocardial wall recorded with high radiation intensity in a short axis representation;

FIG. 2b shows a reconstruction of a data record of the myocardial wall recorded with low radiation intensity in a short axis representation;

DETAILED DESCRIPTION OF THE INVENTION

Figure 3:
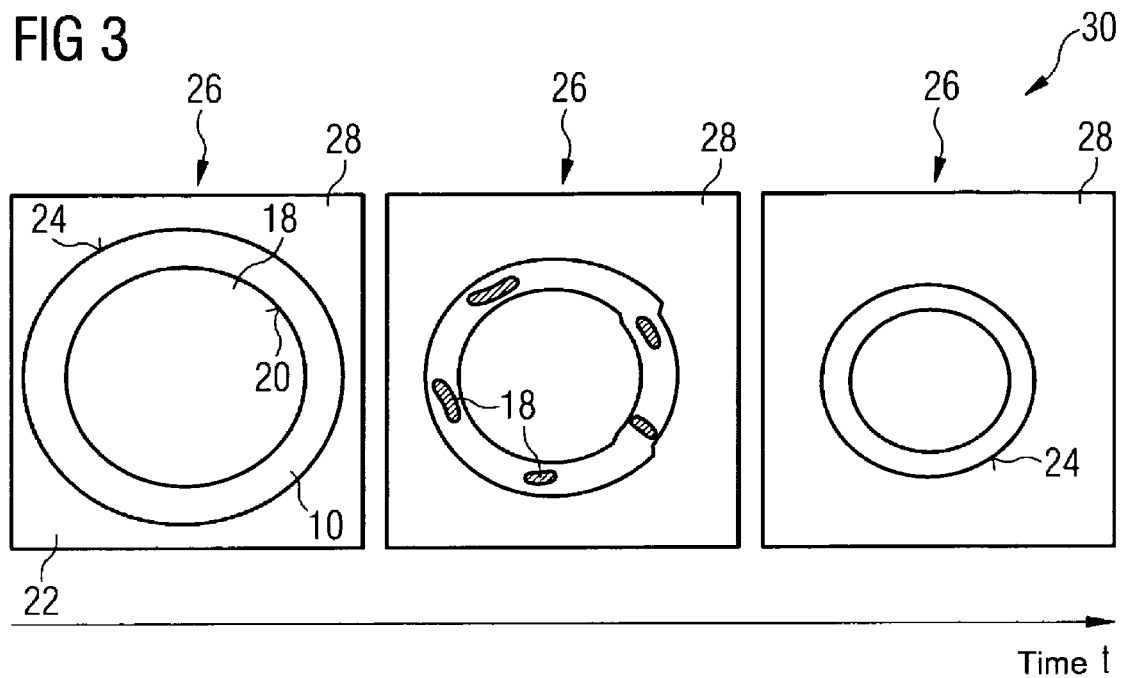
FIG. 3 shows a series of images over time according to an inventive method.

FIG. 1 shows an inventive method 100 for segmenting a myocardial wall 10. A first data record 12, which includes the myocardial wall 10, is recorded using x-ray radiation in a first method step 102. A second data record 12 of the myocardial wall 10 is recorded in the same cardiac phase. The two data records 12, 14 are recorded by an x-ray radiation source with differing radiation intensities as a detector transilluminates a person. Recording with ECG control allows the data records 12, 14 to be recorded in the same cardiac phase. Alternatively the second data record 14 is recorded at the same time as the first data record 12 using a second x-ray radiation source and assigned detector.

The data records 12, 14 essentially capture the radiation intensity of x-ray radiation remaining after transillumination and are used in a further method step 104 to reconstruct the myocardial wall 10. A reconstruction generated from the first data record 12 is shown in FIG. 2a. The radiation intensity of the x-ray radiation for recording the first data record 12 is hereby selected so that regions with blood 18 show a high contrast in the reconstruction. Segmentation of an inside 20 (endocardium) and an outside 24 (epicardium) of the myocardial wall 10 is thus possible, with the other regions, e.g. also the surrounding tissue 22, being difficult to distinguish. To improve the contrast, a contrast agent can be introduced into the blood flow during recording of the data record 12 with high radiation intensity.

Complete segmentation of the myocardial wall 10 requires separation of the fatty tissue 16 interspersing the myocardial wall 10 according to a further method step 108. To this end a lower radiation intensity of the x-ray radiation is used when recording the second data record 14. A slice recording of the corresponding reconstruction with the myocardial wall 10 is shown in FIG. 2b. The radiation intensity here is reduced so that both fatty tissue 16 and also tissue surrounding the myocardial wall 10, e.g. lung tissue, has a lower x-ray contrast than muscular tissue.

Reconstruction of the myocardial wall 10 in method step 104 is performed by separating the region filled with blood 18 and the outside 24 from the reconstruction of the first data record 12, followed by separation of the regions between the endocardium 20 and epicardium 24 of the second data record 14. Essentially an image 26 is generated with the region of the reconstruction of the second data record 14, which is assigned to neither the surrounding tissue 22 nor the region filled with blood 18. To this end the reconstructions of the two data records 12 and 14 have in some instances to be registered and scaled, if this has not already been done, as shown by comparing FIG. 2a and FIG. 2b. If the first and second data records 12, 14 are recorded isocentrically, their registration can be effected particularly simply.

FIG. 2 gives an impression of the size and form of the myocardial wall 10, with the fatty tissue 16 being highlighted in particular or being omitted in the image 26. When the myocardial wall 10 is segmented by reconstructing the image 26 in the form of a short-axis segment 28 the wall thickness in particular can be read. A corresponding image 26 is shown on the left of FIG. 3. Visualization of the pure muscle mass allows conclusions to be drawn about perfusion and therefore the pump function of the myocardial wall 10.

To determine a beat volume, a series of first and second data records 12, 14 is recorded in different cardiac phases. By reconstructing a number of images 26, as shown in FIG. 3, it is possible to calculate volume very accurately over at least one cardiac phase. Also wall movement can be resolved over time. It is also possible in this process to visualize areas of the myocardial wall 10, which contract to a greater or lesser degree over the cardiac phase.

By adding information from the first data record 12, which in particular shows regions filled with blood 18 with a high contrast, it is possible to visualize perfusion of the myocardial wall 10 at a specific point in time. This is shown schematically in the center of FIG. 3.

By tracking any one point in the images 26, marked here by a cross, it is possible to generate a movement profile 54, which can be stored by an inventive device 50 for detecting a coronary artery A with pathological changes.

Figure 4:
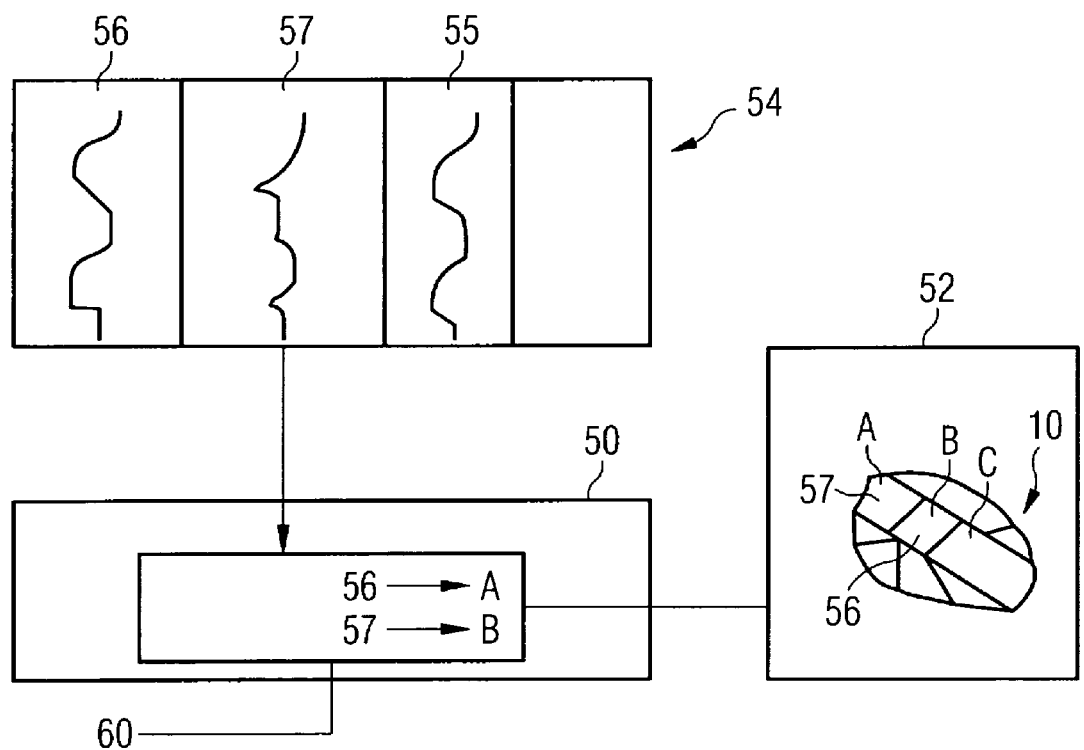
FIG. 4 shows a schematic functional view of an inventive device.

As shown in FIG. 4, the device 50 has an image 52 of the coronary arteries A, B, C. A myocardial wall 10 segmented according to the method 100 described above is divided into segments 56, 57. The device 50 has an assignment of the coronary artery A to the segment 57, which can be derived from the image 52. The coronary artery B is assigned to the segment 56. By tracking a wall movement over time, it is possible to generate a movement profile 54 of the segments 56, 57 respectively. By comparing the movement profiles 54 of each segment 56, 57 with another movement profile, for example a movement profile 55, it is possible to separate a differing movement profile 54 of the segment 57. The coronary artery A supplying the separated segment 57 is marked in color or by an arrow in the image 52.

The movement profile 52 used for the comparison is a movement profile 54 simulated from an anatomical viewpoint. This simulation for example takes into account a blood supply from the assigned coronary artery A influencing the wall movement of the segment 57. A movement profile 55, originating for example from a segment of the myocardial wall 10 from an earlier segmentation or corresponding data, is also stored by the device 50. The marker in the image 52 allows a specific branch to be assigned, which may currently be responsible for a flatter movement profile 56, 57 of a segment. The stored movement profile 55 of a different person can also be stored for comparison purposes. Naturally the segments 56, 57 of the myocardial wall 10 should be compared when the person is subject to physical strain.

The image 52 can be generated using an x-ray tomograph 60, which can also be used to record a first and second data record 12, 14.

The method described above eliminates the disadvantages set out above when visualizing detailed information about the myocardial wall, in particular for cardiological examinations. The accuracy of the examination is enhanced in that segmentation is significantly more reliable due to the parallel processing of two data records. Reduced perfusion and weaker wall movements can thus be identified in a significantly more reliable manner.

The inventive device increases the probability of discovering pathological changes. Marking coronary arteries in segments with an unusual movement profile saves time and therefore cost.

The described concentration on symptomatic coronary arteries also means a higher probability of discovery. Parallel processing of the data records allows reliable segmentation of the myocardium. Symptoms of the myocardium, such as restricted wall movement or perfusion, have to be visualized in this process. This allows automatic detection of pathological changes in the coronary arteries to be determined. This has the advantage that pathological changes can be identified at an extremely early stage. This early identification allows corresponding treatment to be started and complete recovery of the patient to be achieved, the patient's ability to work to be restored or maintained and cost-intensive later treatments to be avoided.

The invention claimed is:

1. A method for segmenting a myocardial wall in an image, comprising:
   recording a first data record of the myocardial wall in a cardiac phase with a first radiation intensity;
   recording a second data record of the myocardial wall in the cardiac phase with a second radiation intensity lower than the first radiation intensity;
   reconstructing the myocardial wall in the image from the first data record and the second data record;
   segmenting an inside and an outside of the myocardial wall from the reconstruction of the first data record; and
   segmenting tissue interspersing the myocardial wall between the inside and the outside of the myocardial wall from the reconstruction of the second data record.

2. The method as claimed in claim 1, wherein the myocardial wall is reconstructed in a longitudinal, or a short axis cross-section, or a polar map.

3. The method as claimed in claim 1, wherein a series of first data are recorded in different cardiac phases with the first radiation intensity.

4. The method as claimed in claim 3, wherein a series of second data records are recorded in the same different cardiac phases with the second radiation intensity.

5. The method as claimed in claim 1, wherein the tissue is a fatty tissue.

6. A device for segmenting a myocardial wall in an image, comprising:
   an image recording device that:
      records a first data record of the myocardial wall in a cardiac phase with a first radiation intensity, and
      records a second data record of the myocardial wall in the cardiac phase with a second radiation intensity lower than the first radiation intensity; and
   a computer that:
      reconstructs the myocardial wall in the image from the first data record and the second data record,
      segments an inside and an outside of the myocardial wall from the reconstruction of the first data record, and
      segments tissue interspersing the myocardial wall between the inside and the outside of the myocardial wall from the reconstruction of the second data record.

7. A device for detecting a pathological change of a coronary artery of a patient, comprising:
- an image recording device that:
  - records a first data record of a myocardial wall in a cardiac phase with a first radiation intensity, and
  - records a second data record of the myocardial wall in the cardiac phase with a second radiation intensity lower than the first radiation intensity; and
- a computer that:
  - reconstructs the myocardial wall from the first data record and the second data record,
  - segments an inside and an outside of the myocardial wall from the reconstruction of the first data record, and
  - segments tissue interspersing the myocardial wall between the inside and the outside of the myocardial wall from the reconstruction of the second data record,
  - assigns the coronary artery to the segment,
  - generates a movement profile for the segment of the myocardial wall over the cardiac phase, and
  - detects the pathological change of the coronary artery based on the movement profile.

8. The device as claimed in claim 7, wherein the pathological change of the coronary artery is detected by comparing the movement profile with a further movement profile.

9. The device as claimed in claim 8, wherein the further movement profile corresponds to a movement profile of an adjacent segment of the myocardial wall or a stored movement profile.

10. The device as claimed in claim 9, wherein the stored movement profile is generated by simulating a movement of the segment of the myocardial wall over the cardiac phase.

11. The device as claimed in claim 9, wherein the stored movement profile is a movement profile of a segment of a myocardial wall of another patient.

12. The device as claimed in claim 9, wherein the stored movement profile is a previously generated segment of the myocardial wall of the patient.

* * * * *